United States Patent [19]

Tarbet

[11] 4,074,940

[45] Feb. 21, 1978

[54] SAMPLE CELL FOR USE IN THE OPTICAL ANALYSIS OF LIQUIDS

[75] Inventor: Cecil Sidney Charles Tarbet, Cambridge, England

[73] Assignee: Cecil Instruments Manufacturing Limited, Cambridge, England

[21] Appl. No.: 670,559

[22] Filed: Mar. 26, 1976

[30] Foreign Application Priority Data

Mar. 27, 1975  United Kingdom ............... 12980/75
Nov. 7, 1975   United Kingdom ............... 46141/75

[51] Int. Cl.² ............................................. G01N 1/10
[52] U.S. Cl. .................................... 356/246; 356/181; 250/576
[58] Field of Search ............... 356/180, 181, 208, 246; 250/576

[56] References Cited

U.S. PATENT DOCUMENTS

| 2,691,737 | 10/1954 | Holby | 250/576 |
| 3,614,452 | 10/1971 | Felton | 356/181 |
| 3,926,526 | 12/1975 | Weiss | 356/181 |

*Primary Examiner*—Vincent P. McGraw
*Attorney, Agent, or Firm*—Brisebois & Kruger

[57] ABSTRACT

A sample cell for use in spectrophotometry has a center-fed horizontal sample bore and exit ducts of reduced cross-sectional area leading away from the ends of the sample bore. In the disclosure, the cross-sectional area of the exit ducts increases downstream of the sample bore and the two exit ducts are joined by a horizontal bore parallel to the sample bore. The hydrostatic head of pressure downstream of the sample bore is minimized by arranging the outlet from the cell well below the inlet. The disclosed cell has low cross-contamination and drift figures, and is substantially immune from trapping of entrained bubbles even when used for discrete sampling.

12 Claims, 3 Drawing Figures

SAMPLE CELL FOR USE IN THE OPTICAL ANALYSIS OF LIQUIDS

BACKGROUND OF THE INVENTION

In the past, sample cells for use in the optical analysis of liquids have been constructed with ever decreasing volume in order to improve the handling of small-volume samples with respect to cross-contamination of the sample by the fraction of a prior sample remaining in the cell. Recently, sample cells with a sample volume of around 75µl have been constructed, but while these have been reasonably satisfactory with an uninterrupted flow of sample liquid, their use for discrete sampling, in which air bubbles are likely to be entrained between the intake of successive samples, has been poor because of the trapping of bubbles in the sample volume and the consequent gross errors in readings. Furthermore, even when bubble-trapping does not occur, the performance of the known cells when handling very small samples, sometimes as small as 500µl in pediatric work, has been less than completely satisfactory.

SUMMARY OF THE INVENTION

The invention has for its object the provision of a sample cell having cross-contamination performance better than 1%, and preferably of the order of 0.1%, in a sample volume not greater than 1,000µl with a substantial immunity from bubble trapping in the sample volume when used for discrete sampling. It is believed that the present invention represents the first achievement of this order of performance.

According to the invention I provide a liquid sample cell for discrete sampling which comprises a body provided with flow passages including the following portions:
a. a generally horizontal bore,
b. an inlet bore extending generally vertically downwardly to meet the horizontal bore at the mid-point of the latter, and
c. a pair of exit ducts each communicating with a corresponding end of the transverse bore and having a cross-section appreciably less than that of the transverse bore.

DESCRIPTION OF THE PREFERRED EMBODIMENT

Figure 1:
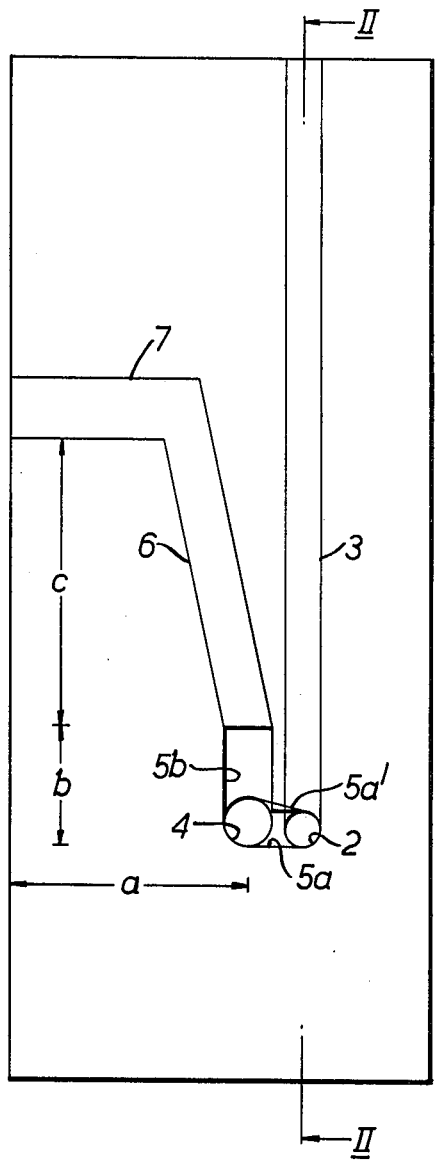
FIG. 1 is a side elevation of a sample cell constructed according to the invention.
Figure 2:
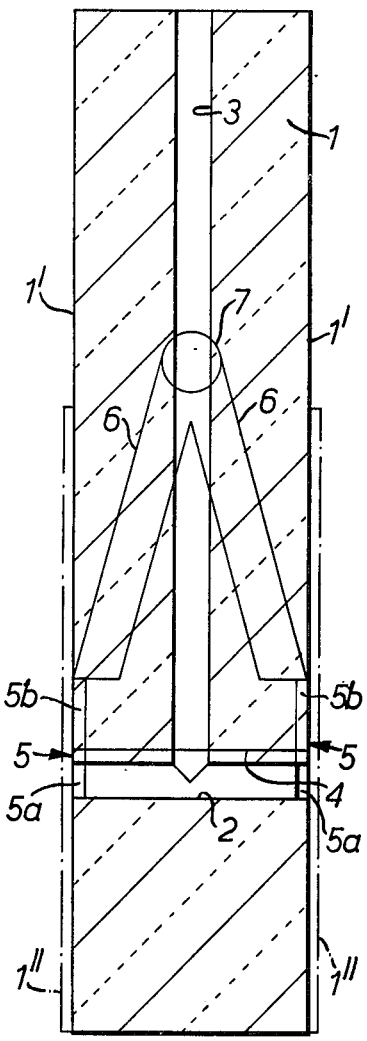
FIG. 2 is a section taken on the line II—II of FIG. 1.

The cell illustrated in FIGS. 1 and 2 is formed from a block 1 of transparent material of rectangular prismatic shape 18 mm by 10 mm in cross-section and 42 mm in height. A transverse bore 2, 1.5 mm in diameter, is bored horizontally through the block, and an inlet bore 3, 1.5 mm in diameter, extends vertically downwardly from the upper surface of the block to meet the upper part of the transverse bore 2 at its mid-point. A second bore 4, 2 mm in diameter extends through the block parallel to the transverse bore 2. The lowermost generators of the two bores are on the same level, and at a distance of 2.25 mm from each other. A pair of exit ducts 5 connect the two ends of the transverse bore 2 to the lower ends of a corresponding pair of inclined bores 6 which meet within the block 1 and communicate with a horizontal outlet bore 7. Each of the exit ducts 5 consists of two sections, cut into the opposed surfaces 1' of the block to a depth of 0.5 mm. The first section 5a extends horizontally to meet the corresponding end of the bore 4, while the second section 5b extends vertically from the end of the bore 4 to meet the corresponding bore 6. As will be seen from the geometric relationship between the exit ducts 5 and the two parallel bores, the sections 5a are 1.5 mm wide and the sections 5b are 2 mm wide. Cover slips 1" are secured to the opposed faces 1' of the block to seal the cell.

Figure 3:
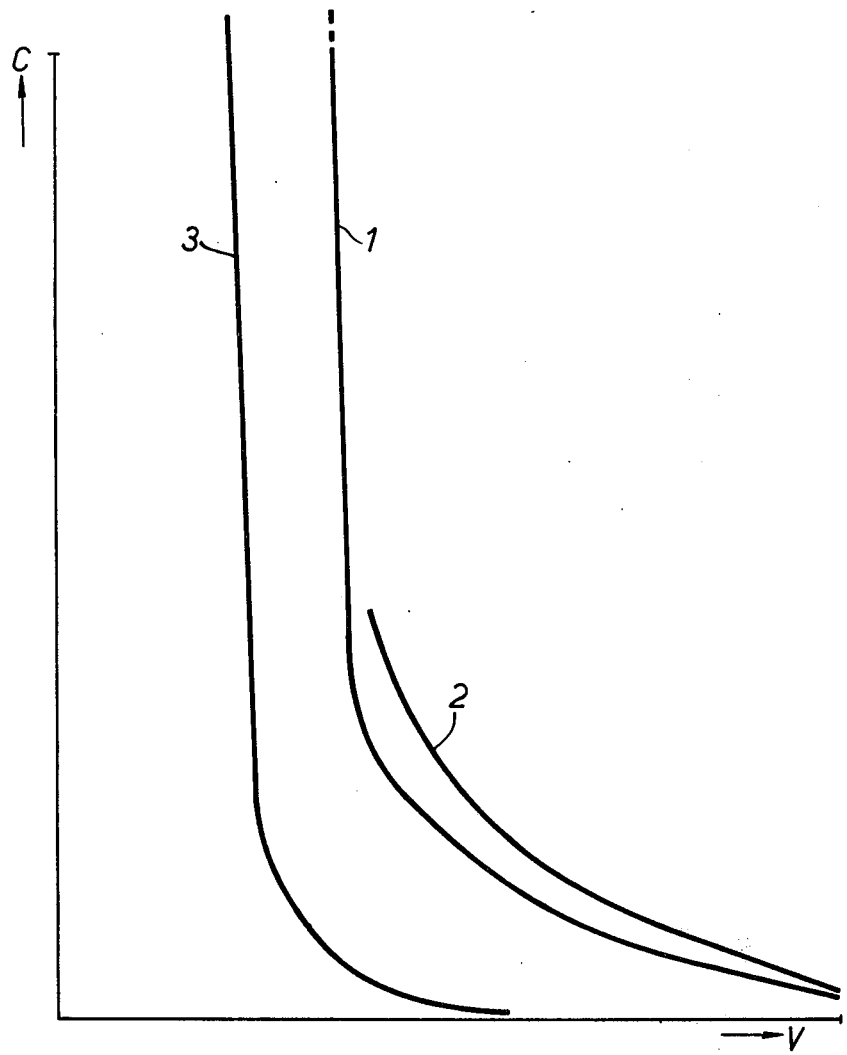
FIG. 3 is a graph showing the performance of the cell of FIGS. 1 and 2 in comparison with that of a known cell.

FIGS. 1 and 2 are drawn to scale, and the marked dimensions are as follows:
A: 10 mm
B: 5 mm
C: 12 mm The approximate volumes of various parts of the cell are as follows:
Inlet bore 3: 56.5µl
Transverse bore 2: 17.6µl
Section 5a: 0.7µl
Section 5b: 3.0µl
Transverse bore 4: 31.4µl
Bores 6 and 7: 120.0µl The cell illustrated in FIGS. 1 and 2 is preferably used with the bore 2 in the optical path of an optical analytical instrument. It has been found that with such an arrangement remarkably low cross-contamination figures can be obtained no doubt due to the very low volume of the bore 2. However, in contrast to known cells having sample bores of relatively low volumes, typically 75µ, little trouble has been experienced with accumulation of air bubbles in the bore when operating by discrete sampling. The cross-contamination performance in comparison with known cells is illustrated by the graph of FIG. 3, which represents the typical result of experiments on the illustrated cell and a known cell of 75µ sample bore volume. The experiment consisted in charging the cell with a solution of potassium permanganate, and then drawing water incrementally into the system and measuring the falling concentration of potassium permanganate in the liquid in the bore 2 at each step. The horizontal axis V of the graph represents the volume of water which had passed into the cell, expressed in ml. on a linear scale extending from zero at the origin to 2.0 ml. at the extreme right, while the vertical axis C represents the cross-contamination of potassium permanganate in the rinsing water in terms of percentage, extending from zero at the origin to 5.0% at the upper limit of the axis also on a linear scale. The curve 1 represents the performance of the known cell, with readings taken immediately upon the intake of water. The curve 2 represents the performance of the known cell when a time-lag of 10 seconds intervened between the intake of water and the taking of readings. The curve 3 represents the performance of the cell of the present invention, and it is to be noted that there was no drift of readings when a time lag was introduced after the intake of water. In the case of curve 3, a cross-contamination figure of 1% corresponds to an intake of 500µ of water. In the case of the known cell, the figure of 1% corresponds to 980µ without time-lag (curve 1) and 1,110µ if allowance is made for 10 seconds delay (curve 2). Although not included within the range of the graph, the cross-contamination on curve 1 for a figure of 500μ was found to be 20%.

The significance of the results discussed above will be appreciated when it is observed that optical analysis of liquids in such fields as pediatrics is nowadays required to be carried out with liquid samples whose volume may be as little as 500μ. The cell tested in curve 1, which may be regarded as a good specimen of its type, is clearly not able to operate on such a small sample with accuracy better than some 10% or so, because of the effects of cross-contamination from the prior contents of the cell. If time lags are allowed during use of the cell, as shown in curve 2, this figure will not be improved, and may get appreciably worse. As far as is known, the cell of the present invention is the only cell suitable for discrete sampling with a performance significantly better than a cross-contamination of 1% with a sample size of 1 ml. or less. It will be seen from an inspection of FIG. 3 that the cross-contamination at a sample volume of 1,000μ is in fact 0.1%.

It appears that the low cross-contamination figure arises basically from the very small volume of the bore 2, which is swept by some 28 changes of liquid in a sample of 500μ. The absence of drift when a time-lag is introduced between sampling and reading is due to the limited amount of reverse movement of the prior sample into the bore 2, and this will be influenced by the small cross-sectional area (0.75 sq. mm.) of the sections 5a and the presence of the relatively large reservoir provided by the transverse bore 4. Another factor in limiting reverse movement is the limited volume and head of pressure downstream of the transverse bore 2. The good degree of immunity to bubble trapping appears to arise from the design of the exit ducts 5, in which the increase of cross-section from 5a (0.75 sq. mm.) to 5b (1.00 sq. mm.) imposes a flow pattern which tends to sweep bubbles away from the transverse bore 2. It is considered that improved results can occur if the sections 5a are flared slightly as indicated by the dotted line 5a¹ in FIG. 1. This again enhances the flow pattern adjacent the ends of the bore 2. Furthermore, the subsequent increase in cross-sections from 5b to the inclined passageways 6 aids in transporting entrained bubbles away from the lower part of the cell. The transverse bore 4 may also play a part in this aspect of performance, since it acts to equalise the pressures at the exit duct sections 5a, thereby tending to ensure that bubbles are swept evenly from both ends of the bore 2. Under normal working conditions it was found that less than 0.5% of all readings taken were influenced in any way by bubble-trapping in the bore 2.

I claim:

1. A liquid sample cell for discrete sampling which comprises a body formed with internal surfaces defining liquid flow passages, said internal surfaces including portions specifically defining:
    a. a generally horizontal sample bore
    b. an inlet bore meeting said sample bore at the midpoint of the latter
    c. a pair of exit ducts each communicating with a corresponding end of said sample bore
    d. a reservoir bore interconnecting said two exit ducts, and
    e. a common outlet duct communicating with said exit ducts at respective points located downstream of their connections to said reservoir bore.

2. A liquid sample cell according to claim 1 wherein said internal surfaces are so arranged that each exit duct defined thereby increases in cross-section in a downstream direction.

3. A liquid sample cell according to claim 2 wherein internal surfaces define each of said exit ducts in two distinct sections.

4. A liquid sample cell according to claim 3 wherein said internal surfaces defining each of said exit ducts define within each exit duct two distinct sections each of constant cross-section.

5. A liquid sample cell according to claim 4 wherein said two distinct sections are defined between vertical internal surfaces lying in common vertical planes.

6. A liquid sample cell according to claim 5 wherein the first of said two sections is defined as a generally horizontal extending passage and the second of said two sections is defined as a generally vertical passage.

7. A liquid sample cell according to claim 4 wherein said internal surfaces define said exit ducts in the form of narrow slots.

8. A liquid sample cell according to claim 1 wherein said internal surfaces further include portions defining a common outlet duct communicating with said exit ducts.

9. A liquid sample cell according to claim 8 wherein said internal surfaces include portions defining inclined passageways providing the communication between said exit ducts and said common outlet duct.

10. A liquid sample cell according to claim 9 wherein said inclined passageways are defined in a common plane inclined to the vertical.

11. A liquid sample cell according to claim 1 wherein the diameter of said reservoir bore is larger than the diameter of said sample bore.

12. A liquid sample cell according to claim 1 wherein the cross-sectional area of each of said exit ducts at its junction with said sample bore is smaller than that of said sample bore.

* * * * *